United States Patent [19]

Shiba et al.

[11] 4,317,771

[45] Mar. 2, 1982

[54] MURAMYLDIPEPTIDE DERIVATIVES

[75] Inventors: Tetsuo Shiba, Toyonaka; Shozo Kotani, Minoo; Yuichi Yamamura, Takarazuka; Osamu Nagase; Hidemasa Ogawa, both of Tokyo, all of Japan

[73] Assignee: Daiichi Seiyaku Co., Ltd., Tokyo, Japan

[21] Appl. No.: 162,233

[22] Filed: Jun. 23, 1980

[30] Foreign Application Priority Data

Jun. 21, 1979 [JP] Japan .................................. 54-78317

[51] Int. Cl.³ ..................... C07C 103/52; A61K 39/00
[52] U.S. Cl. ........................... 260/112.5 R; 424/177; 424/88
[58] Field of Search ..................... 424/177, 85, 88–92; 260/112.5 R

[56] References Cited

U.S. PATENT DOCUMENTS 4,220,637 9/1980 Audibert et al. ............ 260/112.5 R

OTHER PUBLICATIONS

Derwent Abstracts No. 41683, Belgium Pat. No. 849214, 1977.
Chedid, L., et al., Proc. Natl. Acad. Sci., vol. 74, pp. 2089–2093, 1977.

Primary Examiner—Blondel Hazel
Attorney, Agent, or Firm—Sughrue, Mion, Zinn, Macpeak and Seas

[57] ABSTRACT

Muramyldipeptide derivatives of the formula (I):

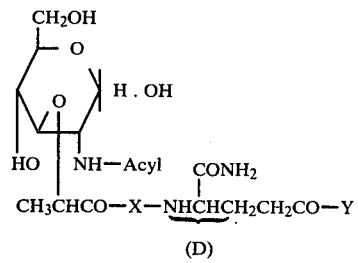

wherein X represents an amino acid residue such as of L-alanine, L-serine, L-valine, glycine, etc., and Y represents a group

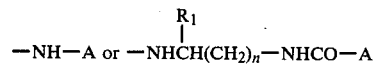

wherein $R_1$ represents a hydrogen atom, an alkyl group of 1 to 6 carbon atoms, a carboxamide group or a carboxyl group, n represents an integer of 1 to 6, A represents a straight or branched chain, saturated or unsaturated aliphatic hydrocarbon residue of 7 to 30 carbon atoms, and "Acyl" means an acyl group of an aliphatic carboxylic acid having 2 to 6 carbon atoms. These compounds have excellent adjuvant activity and/or prophylactic and therapeutic effects against microbial infections.

10 Claims, No Drawings

MURAMYLDIPEPTIDE DERIVATIVES

BACKGROUND OF THE INVENTION

1. Field of the Invention

The present invention relates to novel muramyldipeptide derivatives which have excellent adjuvant activity and/or prophylactic and therapeutic effects against microbial infections and, in particular, this invention relates to a muramyldipeptide derivative of the formula (I):

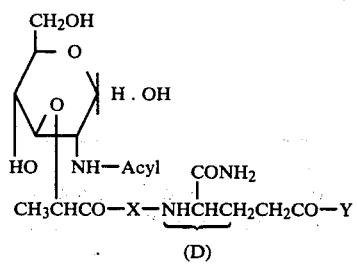

wherein X represents an amino acid residue such as of L-alanine, L-serine, L-valine, glycine, etc., and Y represents a group

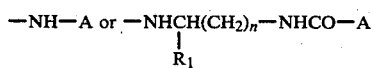

wherein $R_1$ represents a hydrogen atom, an alkyl group of 1 to 6 carbon atoms, a carboxamide group or a carboxyl group, n represents an integer of 1 to 6, A represents a straight or branched chain, saturated or unsaturated aliphatic hydrocarbon residue of 7 to 30 carbon atoms, and "Acyl" means an acyl group of an aliphatic carboxylic acid having 2 to 6 carbon atoms.

That is, the compounds in accordance with the present invention are characterized in that the terminal amino acid group (isoglutamine) is peptide-bonded with an alkylamino group (—NH—A) or an alkyldiamino group in which one of the amino groups is acylated

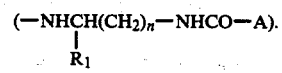

2. Description of the Prior Art

In recent years, through observations on the developments and prognoses of patients who have fallen into leukemia, malignant lymphocytoma, various carcinomatous diseases or even metabolic insufficiency of the organs, there has been revealed a tendency towards frequent occurrence of microbial infections, especially those complicated with intractable diseases (especially, cases of their agonal infections).

In spite of the development of bacteriological screening, adequate attention to therapeutic activities, improvement of prophylactic techniques against infections and moreover widely spread use of various chemotherapeutic agents, there are deaths resulting from general infections and intractable diseases. Such situation is caused by the injury of the resistant factors against infections, e.g., various phagocytes including polymorphocytes. The injury of the resistant factors is due to not only the reduction in defensive ability of the host against the infection itself but also iatrogenic factors such as antitumor agents, immunosuppressive agents, adrenocortical agents, etc. Accordingly, it has been increasingly sought to develop drugs which have prophylactic and therapeutic effects against the aforedescribed infections. However, under the present situation that the occurrence of resistant bacteria resulting from frequent use of chemotherapeutic agents and the treatment of infections using weakly toxic bacteria developed by the bacteria exchange phenomenon have become a trouble, there is a great demand for the development of a novel type of drugs which have no direct bactericidal effect and possess prophylactic and therapeutic effects against infections.

There are a few examples hereto known as those exhibiting such actions and effects, i.e., bacterial whole cells, cell wall skeleton, and extracted substances such as lipopolysaccharide or cord factor, which are derived from some species of microorganisms, namely, Mycobacterium, Corynebacterium, Streptococcus, Listeria, and etc. However, these were not permitted to be administered to human because of their side effects such as their own immunogenicity (antigenicity), pyrogenicity, etc.

In addition, it has been reported that N-acetylmuramyl-L-alanyl-D-isoglutamine (hereinafter referred to as "muramyldipeptide") has defensive effect against certain bacterial infections (Proc. Natl. Acad. Sci. USA Vol. 74, No. 5, pp. 2089-2093). However, the effect exhibited by the above compound is not fully satisfactory. Also, PCT WO 79/00802 discloses some muramyldipeptide derivatives but these compounds are different from the compounds of this invention in the structure.

SUMMARY OF THE INVENTION

As a result of our extensive studies on compounds which can be administered particularly to human and exhibit excellent prophylactic and therapeutic effects, we have found that the compounds of the above formula (I) have excellent prophylactic and therapeutic effects against microbial infections and/or adjuvant activity and thus accomplished the present invention.

DETAILED DESCRIPTION OF THE INVENTION

The effects of the compounds of the present invention were confirmed by the methods described below.

(1) Prophylactic Effect against Microbial Infection

Twenty Std-ddY mice (26 g±1 g, 5 weeks old) per each group were administered subcutaneously with 0.1 mg each of Compounds 1 to 7 of the present invention and Control Compounds 1 to 4, and 24 hours later, the mice were infected subcutaneously with E. coli E 77156 strain at inoculum of $6 \times 10^6$, $9 \times 10^6$ and $1.2 \times 10^7$ cells/mouse, respectively. The effect was judged from the percent survival of the mice seven days after the infection. As clear from the results given in Table 1, the compounds of the present invention showed excellent prophylactic effect against the infection.

TABLE 1

| Prophylactic Effect in Mice Infected with E. coli E77156 | | | | |
|---|---|---|---|---|
| | | % Survival 7 Days after Infection* | | |
| | No. of | Inoculum Size (cells/mouse) of E. coli E77156 | | |
| Test Compound | Mice Used | $6 \times 10^6$ | $9 \times 10^6$ | $1.2 \times 10^7$ |
| Control | | | | |

TABLE 1-continued

Prophylactic Effect in Mice Infected with E. coli E77156

| Test Compound | No. of Mice Used | % Survival 7 Days after Infection* Inoculum Size (cells/mouse) of E. coli E77156 | | |
|---|---|---|---|---|
| | | $6 \times 10^6$ | $9 \times 10^6$ | $1.2 \times 10^7$ |
| Compound 1 | 20 | 60 | 40 | 30 |
| Control Compound 2 | 20 | 50 | | 20 |
| Control Compound 3 | 20 | 40 | | 10 |
| Control Compound 4 | 20 | 45 | | 15 |
| Compound of the Invention 1 | 20 | 70 | 50 | 40 |
| Compound of the Invention 2 | 20 | 80 | 60 | 45 |
| Compound of the Invention 3 | 20 | 90 | 70 | 55 |
| Compound of the Invention 4 | 20 | 80 | 60 | 45 |
| Compound of the Invention 5 | 20 | 80 | 60 | 50 |
| Compound of the Invention 6 | 20 | 70 | 60 | 50 |
| Compound of the Invention 7 | 20 | 80 | 60 | 50 |

*The percent survival shows the difference between the group treated with the compound shown in the Table and the non-treated group.

(2) Adjuvant Activity

According to the method designed by the coinventor, Kotani, et al. (Biken Journal, Vol. 20, 95–103, 1977), the corneal test which is one of the index for adjuvant activity was conducted using guinea pigs. The results, as shown in Table 2, demonstrate that the compounds of the present invention exhibited adjuvant activity comparable with or better than that of the muramyldipeptide.

TABLE 2

| Test Compound | Corneal Test Dosage (μg per guinea pig) | Index of Corneal Reaction |
|---|---|---|
| None | 0 | 0.1 |
| Control Compound 2 | 100 | 0.4 |
| Compound of the Invention 1 | 152 | 0.9 |
| Compound of the Invention 2 | 163 | 1.4 |
| Compound of the Invention 3 | 180 | 1.3 |
| Compound of the Invention 4 | 183 | 1.7 |
| Compound of the Invention 5 | 186 | 1.7 |
| Compound of the Invention 8 | 123 | 0.5 |
| Compound of the Invention 9 | 134 | 0.6 |
| Compound of the Invention 10 | 151 | 0.5 |
| Compound of the Invention 11 | 157 | 0.3 |

Control Compounds 1 to 4 and Compounds 1 to 11 of the present invention shown in Tables 1 and 2 are as follows:

Control Compound 1: $N^\alpha$-(N-Acetylmuramyl-L-alanyl-D-isoglutaminyl)-L-lysine, Control Compound 2: N-Acetylmuramyl-L-alanyl-D-isoglutamine, Control Compound 3: N-Acetylmuramyl-L-seryl-D-isoglutamine, Control Compound 4: N-Acetylmuramyl-L-valyl-D-isoglutamine, Compound 1 of the Invention: $N^\alpha$-(N-Acetyl-muramyl-L-alanyl-D-isoglutaminyl)-$N^\epsilon$-octanoyl-L-lysine, Compound 2 of the Invention: $N^\alpha$-(N-Acetylmuramyl-L-alanyl-D-isoglutaminyl)-$N^\epsilon$-lauroyl-L-lysine, Compound 3 of the Invention: $N^\alpha$-(N-Acetylmuramyl-L-alanyl-D-isogluraminyl)-$N^\epsilon$-stearoyl-L-lysine, Compound 4 of the Invention: $N^\alpha$-(N-Acetylmuramyl-L-seryl-D-isoglutaminyl)-$N^\epsilon$-stearoyl-L-lysine, Compound 5 of the Invention: $N^\alpha$-(N-Acetylmuramyl-L-valyl-D-isoglutaminyl)-$N^\epsilon$-stearoyl-L-lysine, Compound 6 of the Invention: $N^\alpha$-(N-Acetylmuramyl-L-alanyl-D-isoglutaminyl)-$N^\epsilon$-triacontanoyl-L-lysine, Compound 7 of the Invention: $N^\alpha$-(N-Acetylmuramyl-L-alanyl-D-isoglutaminyl)-$N^\epsilon$-isopentadecanoyl-L-lysine, Compound 8 of the Invention: N-Acetylmuramyl-L-alanyl-D-isoglutamine octylamide, Compound 9 of the Invention: N-Acetylmuramyl-L-alanyl-D-isoglutamine laurylamide, Compound 10 of the Invention: N-Acetylmuramyl-L-alanyl-D-isoglutamine stearylamide, and Compound 11 of the Invention: N-Acetylmuramyl-L-valyl-D-isoglutamine stearylamide.

The compounds of the present invention can be produced according to the following reaction scheme:

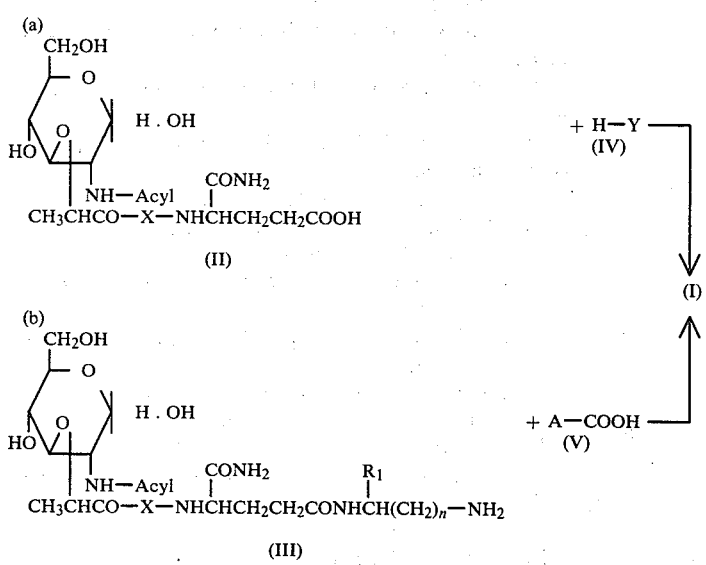

wherein n, Acyl, $R_1$, A, X and Y are as defined above.

More particularly, the compound of the present invention of the formula (I) can be produced either by a method to react a dipeptide of muramic acid (II) with a compound of the formula (IV) (Method a) or by a method to react a tripeptide of muramic acid (III) with a compound of the formula (V) (Method b).

When Method a is employed, the condensation reaction, that is, the reaction of (II)+(IV)→(I), can be chosen from those generally used in peptide synthesis, e.g., carbodiimide method, active ester method, acid anhydride method, etc. For example, the condensation can be conducted by dissolving or suspending compounds of the formulae (II) and (IV) in N,N-dimethylformamide (hereinafter referred to as DMF), tetrahydrofuran or their mixture and reacting them in the presence of (i) a reagent selected from N-hydroxysuccinimide, 1-hydroxybenzotriazole, N-hydroxy-5-norbornene-2,3-dicarboximide, pentachlorophenol, etc., and (ii) a carbodiimide such as dicyclohexyl carbodiimide, 1-ethyl-3-(3-dimethylaminopropyl) carbodiimide or its hydrochloric acid salt generally at room temperature to about 60° C. for about 3 hours to 2 days.

When the condensation reaction of Method b, i.e., the reaction of (III)+(V)→(I), is employed, the reaction conditions used in Method a can be similarly employed. For example, a compound of the formula (V) can be dissolved or suspended in tetrahydrofuran, chloroform or their mixture and reacted with a reagent selected from N-hydroxysuccinimide, 1-hydroxybenzotriazole, N-hydroxy-5-norbornene-2,3-dicarboximide, pentachlorophenol, etc., in the presence of a carbodiimide generally at room temperature to about 60° C. for several hours or overnight to make its active ester of (V), followed by its condensation with a compound of the formula (III).

The condensation reaction can be conducted with stirring in a solvent generally used for peptide synthesis, e.g., DMF, tetrahydrofuran, water, chloroform, etc., alone or as a mixture, at 0° to 60° C., preferably about 25° to 40° C., for several hours to about two days.

The present invention will be illustrated by the following examples and preparation.

EXAMPLE 1

11.4 g of $N^\alpha$-(1-α-O-benzyl-4,6-O-benzylidene-N-acetylmuramyl-L-alanyl-D-isoglutaminyl)-$N^\epsilon$-benzyloxycarbonyl-L-lysine benzyl ester was suspended in 115 ml of 60% acetic acid and heated on a boiling water bath for about an hour. After cooling to room temperature, the reaction mixture was concentrated under reduced pressure and water was added to the residue. The precipitated crystals were collected by filtration and recrystallized from DMF-ethyl acetate to obtain 7.6 g of $N^\alpha$-(1-α-O-benzyl-N-acetylmuramyl-L-alanyl-D-isoglutaminyl)-$N^\epsilon$-benzyloxycarbonyl-L-lysine benzyl ester, m.p. 207°–210° C. (dec.), $[\alpha]_D^{25}+56.6°$ (C=0.3, DMF, 17 hrs. later).

Elemental Analysis for $C_{47}H_{62}O_{14}N_6 \cdot \frac{1}{2}H_2O$,

Calcd. (%): C, 59.80; H, 6.73; N, 8.90,

Found (%): C, 59.65; H, 6.67; N, 8.96.

The compound obtained above was dissolved in about a 20-fold excess of acetic acid and hydrogenolyed in the presence of palladium-carbon in a stream of hydrogen at room temperature. After reaction, the catalyst was filtered off and the filtrate was concentrated under reduced pressure. The residue was purified by chromatography on silica gel using n-butanol-acetic acid-water (4:1:2 by volume) as an eluting solvent. The fractions containing the desired compound were concentrated under reduced pressure and subjected to a basic ion exchange resin (acetate form). The eluate was freeze-dried to obtain $N^\alpha$-(N-acetylmuramyl-L-alanyl-D-isoglutaminyl)-L-lysine.

300 mg of $N^\alpha$-(N-acetylmuramyl-L-alanyl-D-isoglutaminyl)-L-lysine was suspended in 7 ml of DMF and with ice-cooling 148 mg of active N-hydroxy-5-norbornene-2,3-dicarboximide ester of octanoic acid and 0.05 ml of N-methylmorpholine were added thereto. 30 minutes later, the mixture was gradually allowed to warm to room temperature and then stirred overnight. The reaction mixture was concentrated under reduced pressure, and diethyl ether was added to the residue. The precipitated crystals were collected by filtration and then washed successively with diethyl ether and water. Recrystallization from DMF-diethyl ether gave 310 mg of $N^\alpha$-(N-acetylmuramyl-L-alanyl-D-isoglutaminyl)-$N^\epsilon$-octanoyl-L-lysine, m.p. 126° to 130° C. (dec.), $[\alpha]_D^{25}+28.8°$ (C=0.2, DMF, 17 hrs. later).

Elemental Analysis for $C_{33}H_{58}O_{13}N_6.2H_2O$,
Calcd. (%): C, 50.63; H, 7.98; N, 10.74,
Found (%): C, 50.32; H, 7.54; N, 11.00.

The following compounds were prepared in the same manner as above.

$N^\alpha$-(N-Acetylmuramyl-L-alanyl-D-isoglutaminyl)-$N^\epsilon$-lauroyl-L-lysine
m.p. 174.5°–176.5° C. (dec.), $[\alpha]_D^{25}+30.2°$ (C=0.6, DMF, 17 hrs. later).
Elemental Analysis for $C_{37}H_{66}O_{13}N_6.H_2O$
Calcd. (%): C, 54.13; H, 8.35; N, 10.24,
Found (%): C, 53.90; H, 8.40; N, 10.17.

$N^\alpha$-(N-Acetylmuramyl-L-alanyl-D-isoglutaminyl)-$N^\epsilon$-stearoyl-L-lysine
m.p. 175.0°–177.0° C. (dec.), $[\alpha]_D^{25}+25.9°$ (C=0.6, DMF, 17 hrs. later).
Elemental Analysis for $C_{43}H_{78}O_{13}N_6.H_2O$
Calcd. (%): C, 57.06; H, 8.91; N, 9.29,
Found (%): C, 57.21; H, 8.87; N, 9.19.

$N^\alpha$-(N-Acetylmuramyl-L-alanyl-D-isoglutaminyl)-$N^\epsilon$-triacontanoyl-L-lysine
m.p. 165.0°–168° C. (dec.).
Elemental Analysis for $C_{55}H_{102}O_{13}N_6.1-\frac{1}{2}H_2O$,
Calcd. (%): C, 61.03; H, 9.78; N, 7.76,
Found (%): C, 60.89; H, 9.58; N, 7.63.

$N^\alpha$-(N-Acetylmuramyl-L-alanyl-D-isoglutaminyl)-$N^\epsilon$-isopentadecanoyl-L-lysine
m.p. 144.5°–147.5° C. (dec.), $[\alpha]_D^{25}+20.2°$ (C=0.3, DMF, 17 hrs. later).
Elemental Analysis for $C_{40}H_{72}O_{13}N_6$
Calcd. (%): C, 56.85; H, 8.59; N, 9.95,
Found (%): C, 57.26; H, 8.63; N, 9.81.

$N^\alpha$-(N-Acetylmuramyl-L-seryl-D-isoglutaminyl)-$N^\epsilon$-stearoyl-L-lysine
m.p. 175.0°–177.0° C. (dec.), $[\alpha]_D^{25}+27.8°$ (C=0.5, DMF, 17 hrs. later).
Elemental Analysis for $C_{43}H_{78}O_{14}N_6.1-\frac{1}{2}H_2O$,
Calcd. (%): C, 55.52; H, 8.78; N, 9.04,
Found (%): C, 55.46; H, 8.62; N, 9.06.

$N^\alpha$-(N-Acetylmuramyl-L-valyl-D-isoglutaminyl)-$N^\epsilon$-stearoyl-L-lysine
m.p. 182.0°–185.0° C. (dec.), $[\alpha]_D^{25}+22.8°$ (C=0.5, DMF, 17 hrs. later).
Elemental Analysis for $C_{45}H_{82}O_{13}N_6.\frac{1}{2}H_2O$,
Calcd. (%): C, 58.48; H, 9.05; N, 9.09,
Found (%): C, 58.48; H, 8.89; N, 9.12.

EXAMPLE 2

300 mg of N-acetylmuramyl-L-alanyl-D-isoglutamine was dissolved in 2 ml of DMF, to which were added 72 mg of octylamine, 64 mg (0.56 mmol) of N-hydroxysuccinimide and 7 ml of tetrahydrofuran. With ice-cooling and stirring, 115 mg (0.56 mmol) of dicyclohexylcarbodiimide was added thereto. 30 minutes later, the mixture was gradually allowed to warm to room temperature and reacted overnight. The precipitated dicyclohexyl urea was filtered off, the filtrate was concentrated under reduced pressure and water was added to the residue to obtain a precipitate. Recrystallization of the precipitate from DMF-diethyl ether gave 165 mg of N-acetylmuramyl-L-alanyl-D-isoglutamine octylamide, m.p. 174.0°–175.5° C. (dec.), $[\alpha]_D^{25}+30.5°$(C=0.4, acetic acid, 21 hrs. later).

Elemental Analysis for $C_{27}H_{49}O_{10}N_5.H_2O$,
Calcd. (%): C, 52.15; H, 8.26; N, 11.26,
Found (%): C, 51.88; H, 8.00; N, 11.35.

The following compounds were prepared in the same manner as above.

N-Acetylmuramyl-L-alanyl-D-isoglutamine laurylamide
m.p. 186°–187° C. (dec.), $[\alpha]_D^{25}+30.0°$(C=0.5, acetic acid, 21 hrs. later).
Elemental Analysis for $C_{31}H_{57}O_{10}N_5.1-\frac{1}{2}H_2O$,
Calcd. (%): C, 54.20; H, 8.82; N, 10.20,
Found (%): C, 54.43; H, 8.60; N, 9.88.

N-Acetylmuramyl-L-alanyl-D-isoglutamine stearylamide
m.p. 189°–190° C. (dec.), $[\alpha]_D^{25}+28.0°$(C=0.5, acetic acid, 21 hrs. later).
Elemental Analysis for $C_{37}H_{69}O_{10}N_5.\frac{1}{2}H_2O$,
Calcd. (%): C, 59.00; H, 9.39; N, 9.30,
Found (%): C, 58.80; H, 9.37; N, 9.33.

N-Acetylmuramyl-L-valyl-D-isoglutamine stearylamide
m.p. 217°–219°C. (dec.).
Elemental Analysis for $C_{39}H_{73}O_{10}N_5.\frac{1}{2}H_2O$,
Calcd. (%): C, 59.96; H, 9.57; N, 8.97,
Found (%): C, 59.73; H, 9.58; N, 9.16.

PREPARATION

Preparation of an Active Ester of a Fatty Acid 1.0 mmol of a fatty acid was dissolved in 10 ml of tetrahydrofuran, and with ice-cooling and stirring, 206 mg of dicyclohexylcarbodiimide and 179 mg of N-hydroxy-5-norbornene-2,3-dicarboximide were added thereto. 30 minutes later, the mixture was gradually allowed to warm to room temperature and then reacted for 5 hours. The precipitated dicyclohexyl urea was filtered off and the filtrate was concentrated. Dry diethyl ether was added to the residue and the insolubles were filtered off. The filtrate was concentrated under reduced pressure to dryness thereby obtaining active N-hydroxy-5-norbornene-2,3-dicarboximide ester of the fatty acid as white crystals.

In the case of the preparation of active ester of triacontanoic acid, a mixture solvent of tetrahydrofuran and chloroform (1:1 by volume) was employed as a reaction solvent.

While the invention has been described in detail and with reference to specific embodiments thereof, it will be apparent to one skilled in the art that various changes and modifications can be made therein without departing from the spirit and scope thereof.

What is claimed is:

1. A muramyldipeptide derivative of the formula (I):

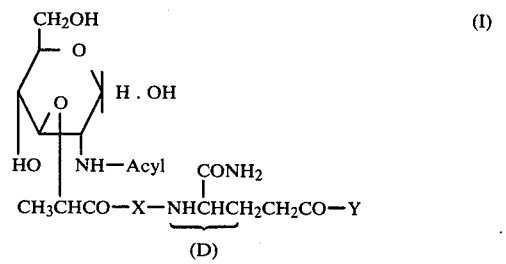

wherein X represents an amino acid residue of L-alanine, L-serine, L-valine or glycine, and Y represents

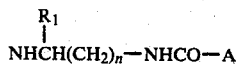

wherein $R_1$ represents a hydrogen atom, an alkyl group of 1 to 6 carbon atoms, a carboxamide group or a carboxy group, n represents an integer of 1 to 6, A represents a straight or branched chain, saturated or unsaturated aliphatic hydrocarbon residue of 7 to 30 carbon atoms, and "Acyl" means an acyl group of an aliphatic carboxylic acid having 2 to 6 carbon atoms.

2. The compound as claimed in claim 1, wherein Y represents a group

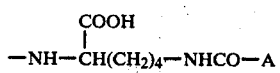

in which A represents a straight, saturated aliphatic hydrocarbon residue of 7 to 30 carbon atoms.

3. The compound as claimed in claim 1, wherein A represents heptadecyl group.

4. The compound as claimed in claim 1, wherein said compound is $N^\alpha$-(N-acetylmuramyl-L-alanyl-D-isoglutaminyl)-$N^\epsilon$-stearoyl-L-lysine.

5. The compound as claimed in claim 1, wherein said compound is $N^\alpha$-(N-acetylmuramyl-L-seryl-D-isoglutaminyl)-$N^\epsilon$-stearoyl-L-lysine.

6. The compound as claimed in claim 1, wherein said compound is $N^\alpha$-(N-acetylmuramyl-L-valyl-D-isoglutaminyl)-$N^\epsilon$-stearoyl-L-lysine.

7. The compound as claimed in claim 1, wherein $R_1$ is a hydrogen atom.

8. The compound as claimed in claim 1, wherein $R_1$ is an alkyl group of 1 to 6 carbon atoms.

9. The compound as claimed in claim 1, wherein $R_1$ is a carboxamide group.

10. The compound as claimed in claim 1, wherein $R_1$ is a carboxy group.

* * * * *